(12) United States Patent
Chin

(10) Patent No.: US 7,477,924 B2
(45) Date of Patent: Jan. 13, 2009

(54) MEDICAL SENSOR AND TECHNIQUE FOR USING THE SAME

(75) Inventor: Rodney Chin, Carson City, NV (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 302 days.

(21) Appl. No.: 11/415,642

(22) Filed: May 2, 2006

(65) Prior Publication Data

US 2007/0260129 A1 Nov. 8, 2007

(51) Int. Cl.
*A61B 5/145* (2006.01)

(52) U.S. Cl. ................................. 600/344; 600/323

(58) Field of Classification Search ............... 600/323, 600/344, 309, 310
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,694,833 A | 9/1987 | Hamaguri |
| 4,697,593 A | 10/1987 | Evans et al. |
| 4,700,708 A | 10/1987 | New, Jr. et al. |

(Continued)

FOREIGN PATENT DOCUMENTS

DE 3405444 8/1985

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner*—Eric F Winakur
*Assistant Examiner*—Etsub D Berhanu
(74) *Attorney, Agent, or Firm*—Fletcher Yoder

(57) ABSTRACT

A medical sensor may be adapted to be affixed to a patient's skin. A sensor for pulse oximetry or other spectrophotometric uses is provided with a gripping region that contacts the patient's skin and provides gripping strength to reduce movement of the sensor. Also provided herein is a method of contacting a sensor to a patient's skin and method of manufacturing a sensor.

39 Claims, 4 Drawing Sheets

U.S. PATENT DOCUMENTS

| | | | |
|---|---|---|---|
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick et al. |
| 5,349,519 A | 9/1994 | Kaestle |

| | | | | | | |
|---|---|---|---|---|---|---|
| 5,349,952 | A | 9/1994 | McCarthy et al. | 5,577,500 A | 11/1996 | Potratz |
| 5,349,953 | A | 9/1994 | McCarthy et al. | 5,582,169 A | 12/1996 | Oda et al. |
| 5,351,685 | A | 10/1994 | Potratz | 5,584,296 A | 12/1996 | Cui et al. |
| 5,353,799 | A | 10/1994 | Chance | 5,588,425 A | 12/1996 | Sackner et al. |
| 5,355,880 | A | 10/1994 | Thomas et al. | 5,588,427 A | 12/1996 | Tien |
| 5,355,882 | A | 10/1994 | Ukawa et al. | 5,590,652 A | 1/1997 | Inai |
| 5,361,758 | A | 11/1994 | Hall et al. | 5,595,176 A | 1/1997 | Yamaura |
| 5,365,066 | A | 11/1994 | Krueger, Jr. et al. | 5,596,986 A | 1/1997 | Goldfarb |
| 5,368,025 | A | 11/1994 | Young et al. | 5,611,337 A | 3/1997 | Bukta |
| 5,368,026 | A | 11/1994 | Swedlow et al. | 5,617,852 A | 4/1997 | MacGregor |
| 5,368,224 | A | 11/1994 | Richardson et al. | 5,619,992 A | 4/1997 | Guthrie et al. |
| 5,372,136 | A | 12/1994 | Steuer et al. | 5,626,140 A | 5/1997 | Feldman et al. |
| 5,377,675 | A | 1/1995 | Ruskewicz et al. | 5,630,413 A | 5/1997 | Thomas et al. |
| 5,385,143 | A | 1/1995 | Aoyagi | 5,632,272 A | 5/1997 | Diab et al. |
| 5,387,122 | A | 2/1995 | Goldberger et al. | 5,632,273 A | 5/1997 | Suzuki |
| 5,390,670 | A | 2/1995 | Centa et al. | 5,634,459 A | 6/1997 | Gardosi |
| 5,392,777 | A | 2/1995 | Swedlow et al. | 5,638,593 A | 6/1997 | Gerhardt et al. |
| 5,398,680 | A | 3/1995 | Polson et al. | 5,638,816 A | 6/1997 | Kiani-Azarbayjany et al. |
| 5,402,777 | A | 4/1995 | Warring et al. | 5,638,818 A | 6/1997 | Diab et al. |
| 5,402,779 | A | 4/1995 | Chen et al. | 5,645,060 A | 7/1997 | Yorkey et al. |
| 5,411,023 | A | 5/1995 | Morris, Sr. et al. | 5,645,440 A | 7/1997 | Tobler et al. |
| 5,411,024 | A | 5/1995 | Thomas et al. | 5,660,567 A | 8/1997 | Nierlich et al. |
| 5,413,099 | A | 5/1995 | Schmidt et al. | 5,662,105 A | 9/1997 | Tien |
| 5,413,100 | A | 5/1995 | Barthelemy et al. | 5,662,106 A | 9/1997 | Swedlow et al. |
| 5,413,101 | A | 5/1995 | Sugiura | 5,664,270 A | 9/1997 | Bell et al. |
| 5,413,102 | A | 5/1995 | Schmidt et al. | 5,666,952 A | 9/1997 | Fuse et al. |
| 5,417,207 | A | 5/1995 | Young et al. | 5,671,529 A | 9/1997 | Nelson |
| 5,421,329 | A | 6/1995 | Casciani et al. | 5,673,692 A | 10/1997 | Schulze et al. |
| 5,425,360 | A | 6/1995 | Nelson | 5,673,693 A | 10/1997 | Solenberger |
| 5,425,362 | A | 6/1995 | Siker et al. | 5,676,139 A | 10/1997 | Goldberger et al. |
| 5,427,093 | A | 6/1995 | Ogawa et al. | 5,676,141 A | 10/1997 | Hollub |
| 5,429,128 | A | 7/1995 | Cadell et al. | 5,678,544 A | 10/1997 | DeLonzor et al. |
| 5,429,129 | A | 7/1995 | Lovejoy et al. | 5,680,857 A | 10/1997 | Pelikan et al. |
| 5,431,159 | A | 7/1995 | Baker et al. | 5,685,299 A | 11/1997 | Diab et al. |
| 5,431,170 | A | 7/1995 | Mathews | 5,685,301 A | 11/1997 | Klomhaus |
| 5,437,275 | A | 8/1995 | Amundsen et al. | 5,687,719 A | 11/1997 | Sato et al. |
| 5,438,986 | A | 8/1995 | Disch et al. | 5,687,722 A | 11/1997 | Tien et al. |
| 5,448,991 | A | 9/1995 | Polson et al. | 5,692,503 A | 12/1997 | Kuenstner |
| 5,452,717 | A | 9/1995 | Branigan et al. | 5,692,505 A | 12/1997 | Fouts |
| 5,465,714 | A | 11/1995 | Scheuing | 5,709,205 A | 1/1998 | Bukta |
| 5,469,845 | A | 11/1995 | DeLonzor et al. | 5,713,355 A | 2/1998 | Richardson et al. |
| RE35,122 | E | 12/1995 | Corenman et al. | 5,724,967 A | 3/1998 | Venkatachalam |
| 5,482,034 | A | 1/1996 | Lewis et al. | 5,727,547 A | 3/1998 | Levinson et al. |
| 5,482,036 | A | 1/1996 | Diab et al. | 5,730,124 A | 3/1998 | Yamauchi |
| 5,485,847 | A | 1/1996 | Baker, Jr. | 5,731,582 A | 3/1998 | West |
| 5,490,505 | A | 2/1996 | Diab et al. | D393,830 S | 4/1998 | Tobler et al. |
| 5,490,523 | A | 2/1996 | Isaacson et al. | 5,743,260 A | 4/1998 | Chung et al. |
| 5,491,299 | A | 2/1996 | Naylor et al. | 5,743,262 A | 4/1998 | Lepper, Jr. et al. |
| 5,494,032 | A | 2/1996 | Robinson et al. | 5,743,263 A | 4/1998 | Baker, Jr. |
| 5,494,043 | A | 2/1996 | O'Sullivan et al. | 5,746,206 A | 5/1998 | Mannheimer |
| 5,497,771 | A | 3/1996 | Rosenheimer | 5,746,697 A | 5/1998 | Swedlow et al. |
| 5,499,627 | A | 3/1996 | Steuer et al. | 5,752,914 A | 5/1998 | Delonzor et al. |
| 5,503,148 | A | 4/1996 | Pologe et al. | 5,755,226 A | 5/1998 | Carim et al. |
| 5,505,199 | A | 4/1996 | Kim | 5,758,644 A | 6/1998 | Diab et al. |
| 5,507,286 | A | 4/1996 | Solenberger | 5,760,910 A | 6/1998 | Lepper, Jr. et al. |
| 5,511,546 | A | 4/1996 | Hon | 5,766,125 A | 6/1998 | Aoyagi et al. |
| 5,517,988 | A | 5/1996 | Gerhard | 5,766,127 A | 6/1998 | Pologe et al. |
| 5,520,177 | A | 5/1996 | Ogawa et al. | 5,769,785 A | 6/1998 | Diab et al. |
| 5,521,851 | A | 5/1996 | Wei et al. | 5,772,587 A | 6/1998 | Gratton et al. |
| 5,522,388 | A | 6/1996 | Ishikawa et al. | 5,774,213 A | 6/1998 | Trebino et al. |
| 5,524,617 | A | 6/1996 | Mannheimer | 5,776,058 A | 7/1998 | Levinson et al. |
| 5,529,064 | A | 6/1996 | Rall et al. | 5,776,059 A | 7/1998 | Kaestle |
| 5,533,507 | A | 7/1996 | Potratz et al. | 5,779,630 A | 7/1998 | Fein et al. |
| 5,551,423 | A | 9/1996 | Sugiura | 5,782,237 A | 7/1998 | Casciani et al. |
| 5,551,424 | A | 9/1996 | Morrison et al. | 5,782,756 A | 7/1998 | Mannheimer |
| 5,553,614 | A | 9/1996 | Chance | 5,782,757 A | 7/1998 | Diab et al. |
| 5,553,615 | A | 9/1996 | Carim et al. | 5,782,758 A | 7/1998 | Ausec et al. |
| 5,555,882 | A | 9/1996 | Richardson et al. | 5,786,592 A | 7/1998 | Hök |
| 5,558,096 | A | 9/1996 | Palatnik | 5,788,634 A | 8/1998 | Suda et al. |
| 5,560,355 | A | 10/1996 | Merchant et al. | 5,790,729 A | 8/1998 | Pologe et al. |
| 5,564,417 | A | 10/1996 | Chance | 5,792,052 A | 8/1998 | Isaacson et al. |
| 5,575,284 | A | 11/1996 | Athan et al. | 5,795,292 A | 8/1998 | Lewis et al. |
| 5,575,285 | A | 11/1996 | Takanashi et al. | 5,797,841 A | 8/1998 | Delonzor et al. |

| | | | | | | |
|---|---|---|---|---|---|---|
| 5,800,348 | A | 9/1998 | Kaestle | 5,995,855 | A | 11/1999 | Kiani et al. |
| 5,800,349 | A | 9/1998 | Isaacson et al. | 5,995,856 | A | 11/1999 | Mannheimer et al. |
| 5,803,910 | A | 9/1998 | Potratz | 5,995,858 | A | 11/1999 | Kinast |
| 5,807,246 | A | 9/1998 | Sakaguchi et al. | 5,995,859 | A | 11/1999 | Takahashi |
| 5,807,247 | A | 9/1998 | Merchant et al. | 5,997,343 | A | 12/1999 | Mills et al. |
| 5,807,248 | A | 9/1998 | Mills | 5,999,834 | A | 12/1999 | Wang et al. |
| 5,810,723 | A | 9/1998 | Aldrich | 6,002,952 | A | 12/1999 | Diab et al. |
| 5,810,724 | A | 9/1998 | Gronvall | 6,005,658 | A | 12/1999 | Kaluza et al. |
| 5,813,980 | A | 9/1998 | Levinson et al. | 6,006,120 | A | 12/1999 | Levin |
| 5,817,008 | A | 10/1998 | Rafert et al. | 6,011,985 | A | 1/2000 | Athan et al. |
| 5,817,009 | A | 10/1998 | Rosenheimer et al. | 6,011,986 | A | 1/2000 | Diab et al. |
| 5,817,010 | A | 10/1998 | Hibl | 6,014,576 | A | 1/2000 | Raley et al. |
| 5,818,985 | A | 10/1998 | Merchant et al. | 6,018,673 | A | 1/2000 | Chin et al. |
| 5,820,550 | A | 10/1998 | Polson et al. | 6,018,674 | A | 1/2000 | Aronow |
| 5,823,950 | A | 10/1998 | Diab et al. | 6,022,321 | A | 2/2000 | Amano et al. |
| 5,823,952 | A | 10/1998 | Levinson et al. | 6,023,541 | A | 2/2000 | Merchant et al. |
| 5,827,179 | A | 10/1998 | Lichter et al. | 6,026,312 | A | 2/2000 | Shemwell et al. |
| 5,827,182 | A | 10/1998 | Raley et al. | 6,026,314 | A | 2/2000 | Amerov et al. |
| 5,829,439 | A | 11/1998 | Yokosawa et al. | 6,031,603 | A | 2/2000 | Fine et al. |
| 5,830,135 | A | 11/1998 | Bosque et al. | 6,035,223 | A | 3/2000 | Baker, Jr. |
| 5,830,136 | A | 11/1998 | Delonzor et al. | 6,036,642 | A | 3/2000 | Diab et al. |
| 5,830,137 | A | 11/1998 | Scharf | 6,041,247 | A | 3/2000 | Weckstrom et al. |
| 5,839,439 | A | 11/1998 | Nierlich et al. | 6,044,283 | A | 3/2000 | Fein et al. |
| RE36,000 | E | 12/1998 | Swedlow et al. | 6,047,201 | A | 4/2000 | Jackson, III |
| 5,842,979 | A | 12/1998 | Jarman et al. | 6,055,447 | A | 4/2000 | Well |
| 5,842,981 | A | 12/1998 | Larsen et al. | 6,061,584 | A | 5/2000 | Lovejoy et al. |
| 5,842,982 | A | 12/1998 | Mannheimer | 6,064,898 | A | 5/2000 | Aldrich |
| 5,846,190 | A | 12/1998 | Woehrle | 6,064,899 | A | 5/2000 | Fein et al. |
| 5,851,178 | A | 12/1998 | Aronow | 6,067,462 | A | 5/2000 | Diab et al. |
| 5,851,179 | A | 12/1998 | Ritson et al. | 6,073,038 | A | 6/2000 | Wang et al. |
| 5,853,364 | A | 12/1998 | Baker, Jr. et al. | 6,078,829 | A | 6/2000 | Uchida |
| 5,860,919 | A | 1/1999 | Kiani-Azarbayjany et al. | 6,078,833 | A | 6/2000 | Hueber |
| 5,865,736 | A | 2/1999 | Baker, Jr. et al. | 6,081,735 | A | 6/2000 | Diab et al. |
| 5,879,294 | A | 3/1999 | Anderson et al. | 6,083,157 | A | 7/2000 | Noller |
| 5,885,213 | A | 3/1999 | Richardson et al. | 6,083,172 | A | 7/2000 | Baker, Jr. et al. |
| 5,890,929 | A | 4/1999 | Mills et al. | 6,088,607 | A | 7/2000 | Diab et al. |
| 5,891,021 | A | 4/1999 | Dillon et al. | 6,094,592 | A | 7/2000 | Yorkey et al. |
| 5,891,022 | A | 4/1999 | Pologe | 6,095,974 | A | 8/2000 | Shemwell et al. |
| 5,891,024 | A | 4/1999 | Jarman et al. | 6,104,938 | A | 8/2000 | Huiku et al. |
| 5,891,025 | A | 4/1999 | Buschmann et al. | 6,104,939 | A | 8/2000 | Groner |
| 5,891,026 | A | 4/1999 | Wang et al. | 6,112,107 | A | 8/2000 | Hannula |
| 5,902,235 | A | 5/1999 | Lewis et al. | 6,113,541 | A | 9/2000 | Dias et al. |
| 5,910,108 | A | 6/1999 | Solenberger | 6,115,621 | A | 9/2000 | Chin |
| 5,911,690 | A | 6/1999 | Rall | 6,122,535 | A | 9/2000 | Kaestle et al. |
| 5,912,656 | A | 6/1999 | Tham et al. | 6,133,994 | A | 10/2000 | Mathews et al. |
| 5,913,819 | A | 6/1999 | Taylor et al. | 6,135,952 | A | 10/2000 | Coetzee |
| 5,916,154 | A | 6/1999 | Hobbs et al. | 6,144,444 | A | 11/2000 | Haworth et al. |
| 5,916,155 | A | 6/1999 | Levinson et al. | 6,144,867 | A | 11/2000 | Walker et al. |
| 5,919,133 | A | 7/1999 | Taylor et al. | 6,144,868 | A | 11/2000 | Parker |
| 5,919,134 | A | 7/1999 | Diab | 6,149,481 | A | 11/2000 | Wang et al. |
| 5,920,263 | A | 7/1999 | Huttenhoff et al. | 6,151,107 | A | 11/2000 | Schöllermann et al. |
| 5,921,921 | A | 7/1999 | Potratz et al. | 6,151,516 | A | 11/2000 | Kiani-Azarbayjany et al. |
| 5,922,607 | A | 7/1999 | Bernreuter | 6,151,518 | A | 11/2000 | Hayashi |
| 5,924,979 | A | 7/1999 | Swedlow et al. | 6,152,754 | A | 11/2000 | Gerhardt et al. |
| 5,924,980 | A | 7/1999 | Coetzee | 6,154,667 | A | 11/2000 | Miura et al. |
| 5,924,982 | A | 7/1999 | Chin | 6,157,850 | A | 12/2000 | Diab et al. |
| 5,924,985 | A | 7/1999 | Jones | 6,159,147 | A | 12/2000 | Lichter |
| 5,934,277 | A | 8/1999 | Mortz | 6,163,715 | A | 12/2000 | Larsen et al. |
| 5,934,925 | A | 8/1999 | Tobler et al. | 6,165,005 | A | 12/2000 | Mills et al. |
| 5,940,182 | A | 8/1999 | Lepper, Jr. et al. | 6,173,196 | B1 | 1/2001 | Delonzor et al. |
| 5,954,644 | A | 9/1999 | Dettling et al. | 6,178,343 | B1 | 1/2001 | Bindszus et al. |
| 5,957,840 | A | 9/1999 | Terasawa et al. | 6,179,159 | B1 | 1/2001 | Gurley |
| 5,960,610 | A | 10/1999 | Levinson et al. | 6,181,958 | B1 | 1/2001 | Steuer et al. |
| 5,961,450 | A | 10/1999 | Merchant et al. | 6,181,959 | B1 | 1/2001 | Schöllermann et al. |
| 5,961,452 | A | 10/1999 | Chung et al. | 6,184,521 | B1 | 2/2001 | Coffin, IV et al. |
| 5,964,701 | A | 10/1999 | Asada et al. | 6,188,470 | B1 | 2/2001 | Grace |
| 5,971,930 | A | 10/1999 | Elghazzawi | 6,192,260 | B1 | 2/2001 | Chance |
| 5,978,691 | A | 11/1999 | Mills | 6,195,574 | B1* | 2/2001 | Kumar et al. ............... 600/323 |
| 5,978,693 | A | 11/1999 | Hamilton et al. | 6,195,575 | B1 | 2/2001 | Levinson |
| 5,983,120 | A | 11/1999 | Groner et al. | 6,198,951 | B1 | 3/2001 | Kosuda et al. |
| 5,983,122 | A | 11/1999 | Jarman et al. | 6,206,830 | B1 | 3/2001 | Diab et al. |
| 5,987,343 | A | 11/1999 | Kinast | 6,213,952 | B1 | 4/2001 | Finarov et al. |
| 5,991,648 | A | 11/1999 | Levin | 6,217,523 | B1 | 4/2001 | Amano et al. |

| | | | | | | |
|---|---|---|---|---|---|---|
| 6,222,189 | B1 | 4/2001 | Misner et al. | 6,438,396 | B1 | 8/2002 | Cook |
| 6,223,064 | B1 | 4/2001 | Lynn | 6,438,399 | B1 | 8/2002 | Kurth |
| 6,226,539 | B1 | 5/2001 | Potratz | 6,449,501 | B1 | 9/2002 | Reuss |
| 6,226,540 | B1 | 5/2001 | Bernreuter et al. | 6,453,183 | B1 | 9/2002 | Walker |
| 6,229,856 | B1 | 5/2001 | Diab et al. | 6,453,184 | B1 | 9/2002 | Hyogo et al. |
| 6,230,035 | B1 | 5/2001 | Aoyagi et al. | 6,456,862 | B2 | 9/2002 | Benni |
| 6,233,470 | B1 | 5/2001 | Tsuchiya | 6,461,305 | B1 | 10/2002 | Schnall |
| 6,236,871 | B1 | 5/2001 | Tsuchiya | 6,463,310 | B1 | 10/2002 | Swedlow et al. |
| 6,236,872 | B1 | 5/2001 | Diab et al. | 6,463,311 | B1 | 10/2002 | Diab |
| 6,240,305 | B1 | 5/2001 | Tsuchiya | 6,466,808 | B1 | 10/2002 | Chin et al. |
| 6,253,097 | B1 | 6/2001 | Aronow et al. | 6,466,809 | B1 | 10/2002 | Riley |
| 6,253,098 | B1 | 6/2001 | Walker et al. | 6,470,199 | B1 | 10/2002 | Kopotic et al. |
| 6,256,523 | B1 | 7/2001 | Diab et al. | 6,470,200 | B2 | 10/2002 | Walker et al. |
| 6,256,524 | B1 | 7/2001 | Walker et al. | 6,480,729 | B2 | 11/2002 | Stone |
| 6,261,236 | B1 | 7/2001 | Grimblatov | 6,490,466 | B1 | 12/2002 | Fein et al. |
| 6,263,221 | B1 | 7/2001 | Chance et al. | 6,493,568 | B1 | 12/2002 | Bell |
| 6,263,222 | B1 | 7/2001 | Diab et al. | 6,496,711 | B1 | 12/2002 | Athan et al. |
| 6,263,223 | B1 | 7/2001 | Shepherd et al. | 6,498,942 | B1 | 12/2002 | Esenaliev et al. |
| 6,266,546 | B1 | 7/2001 | Steuer et al. | 6,501,974 | B2 | 12/2002 | Huiku |
| 6,266,547 | B1 | 7/2001 | Walker et al. | 6,501,975 | B2 | 12/2002 | Diab et al. |
| 6,272,363 | B1 | 8/2001 | Casciani et al. | 6,505,060 | B1 | 1/2003 | Norris |
| 6,278,522 | B1 | 8/2001 | Lepper, Jr. et al. | 6,505,061 | B2 | 1/2003 | Larson |
| 6,280,213 | B1 | 8/2001 | Tobler et al. | 6,505,133 | B1 | 1/2003 | Hanna et al. |
| 6,280,381 | B1 | 8/2001 | Malin et al. | 6,510,329 | B2 | 1/2003 | Heckel |
| 6,285,894 | B1 | 9/2001 | Oppelt et al. | 6,510,331 | B1 | 1/2003 | Williams et al. |
| 6,285,895 | B1 | 9/2001 | Ristolainen et al. | 6,512,937 | B2 | 1/2003 | Blank et al. |
| 6,285,896 | B1 | 9/2001 | Tobler et al. | 6,515,273 | B2 | 2/2003 | Al-Ali |
| 6,298,252 | B1 | 10/2001 | Kovach et al. | 6,519,484 | B1 | 2/2003 | Lovejoy et al. |
| 6,308,089 | B1 | 10/2001 | Von der Ruhr et al. | 6,519,486 | B1 | 2/2003 | Edgar, Jr. et al. |
| 6,321,100 | B1 | 11/2001 | Parker | 6,519,487 | B1 | 2/2003 | Parker |
| 6,330,468 | B1 | 12/2001 | Scharf | 6,525,386 | B1 | 2/2003 | Mills et al. |
| 6,334,065 | B1 | 12/2001 | Al-Ali et al. | 6,526,300 | B1 | 2/2003 | Kiani et al. |
| 6,339,715 | B1 | 1/2002 | Bahr et al. | 6,526,301 | B2 | 2/2003 | Larsen et al. |
| 6,342,039 | B1 | 1/2002 | Lynn | 6,541,756 | B2 | 4/2003 | Schulz et al. |
| 6,343,223 | B1 | 1/2002 | Chin et al. | 6,542,764 | B1 | 4/2003 | Al-Ali et al. |
| 6,343,224 | B1 | 1/2002 | Parker | 6,546,267 | B1 | 4/2003 | Sugiura et al. |
| 6,349,228 | B1 | 2/2002 | Kiani et al. | 6,553,241 | B2 | 4/2003 | Mannheimer et al. |
| 6,351,658 | B1 | 2/2002 | Middleman et al. | 6,553,242 | B1 | 4/2003 | Sarussi |
| 6,353,750 | B1 | 3/2002 | Kimura | 6,553,243 | B2 | 4/2003 | Gurley |
| 6,356,774 | B1 | 3/2002 | Bernstein et al. | 6,554,788 | B1 | 4/2003 | Hunley |
| 6,360,113 | B1 | 3/2002 | Dettling | 6,556,852 | B1 | 4/2003 | Schulze et al. |
| 6,360,114 | B1 | 3/2002 | Diab et al. | 6,560,470 | B1 | 5/2003 | Pologe |
| 6,361,501 | B1 | 3/2002 | Amano et al. | 6,564,077 | B2 | 5/2003 | Mortara |
| 6,363,269 | B1 | 3/2002 | Hanna et al. | 6,564,088 | B1 | 5/2003 | Soller et al. |
| D455,834 | S | 4/2002 | Donars et al. | 6,571,113 | B1 | 5/2003 | Fein et al. |
| 6,370,408 | B1 | 4/2002 | Merchant et al. | 6,571,114 | B1 | 5/2003 | Koike et al. |
| 6,370,409 | B1 | 4/2002 | Chung et al. | 6,574,491 | B2 | 6/2003 | Elghazzawi |
| 6,371,921 | B1 | 4/2002 | Caro | 6,580,086 | B1 | 6/2003 | Schulz et al. |
| 6,374,129 | B1 | 4/2002 | Chin et al. | 6,584,336 | B1 | 6/2003 | Ali et al. |
| 6,377,829 | B1 | 4/2002 | Al-Ali et al. | 6,587,703 | B2 | 7/2003 | Cheng et al. |
| 6,381,479 | B1 | 4/2002 | Norris | 6,587,704 | B1 | 7/2003 | Fine et al. |
| 6,381,480 | B1 | 4/2002 | Stoddart et al. | 6,589,172 | B2 | 7/2003 | Williams et al. |
| 6,385,471 | B1 | 5/2002 | Mortz | 6,591,122 | B2 | 7/2003 | Schmitt |
| 6,385,821 | B1 | 5/2002 | Modgil et al. | 6,591,123 | B2 | 7/2003 | Fein et al. |
| 6,388,240 | B2 | 5/2002 | Schulz et al. | 6,594,511 | B2 | 7/2003 | Stone et al. |
| 6,393,310 | B1 | 5/2002 | Kuenstner | 6,594,512 | B2 | 7/2003 | Huang |
| 6,393,311 | B1 | 5/2002 | Edgar, Jr. et al. | 6,594,513 | B1 | 7/2003 | Jobsis et al. |
| 6,397,091 | B2 | 5/2002 | Diab et al. | 6,597,931 | B1 | 7/2003 | Cheng et al. |
| 6,397,092 | B1 | 5/2002 | Norris et al. | 6,597,933 | B2 | 7/2003 | Kiani et al. |
| 6,397,093 | B1 | 5/2002 | Aldrich | 6,600,940 | B1 | 7/2003 | Fein et al. |
| D458,226 | S | 6/2002 | Chin et al. | 6,606,510 | B2 | 8/2003 | Swedlow et al. |
| 6,400,971 | B1 | 6/2002 | Finarov et al. | 6,606,511 | B1 | 8/2003 | Ali et al. |
| 6,400,972 | B1 | 6/2002 | Fine | 6,606,512 | B2 | 8/2003 | Muz et al. |
| 6,400,973 | B1 | 6/2002 | Winter | 6,608,562 | B1 | 8/2003 | Kimura et al. |
| 6,402,690 | B1 | 6/2002 | Rhee et al. | 6,609,016 | B1 | 8/2003 | Lynn |
| 6,408,198 | B1 | 6/2002 | Hanna et al. | 6,615,064 | B1 | 9/2003 | Aldrich |
| 6,411,832 | B1 | 6/2002 | Guthermann | 6,615,065 | B1 | 9/2003 | Barrett et al. |
| 6,411,833 | B1 | 6/2002 | Baker, Jr. et al. | 6,618,602 | B2 | 9/2003 | Levin et al. |
| 6,421,549 | B1 | 7/2002 | Jacques | 6,622,034 | B1 | 9/2003 | Gorski et al. |
| 6,430,423 | B2 | 8/2002 | DeLonzor et al. | 6,628,975 | B1 | 9/2003 | Fein et al. |
| 6,430,513 | B1 | 8/2002 | Wang et al. | 6,631,281 | B1 | 10/2003 | Kästle |
| 6,430,525 | B1 | 8/2002 | Weber et al. | 6,632,181 | B2 | 10/2003 | Flaherty |
| 6,434,408 | B1 | 8/2002 | Heckel et al. | 6,640,116 | B2 | 10/2003 | Diab |

| Patent | Type | Date | Inventor |
|---|---|---|---|
| 6,643,530 | B2 | 11/2003 | Diab et al. |
| 6,643,531 | B1 | 11/2003 | Katarow |
| 6,647,279 | B2 | 11/2003 | Pologe |
| 6,647,280 | B2 | 11/2003 | Bahr et al. |
| 6,650,916 | B2 | 11/2003 | Cook |
| 6,650,917 | B2 | 11/2003 | Diab et al. |
| 6,650,918 | B2 | 11/2003 | Terry |
| 6,654,621 | B2 | 11/2003 | Palatnik et al. |
| 6,654,622 | B1 | 11/2003 | Eberhard et al. |
| 6,654,623 | B1 | 11/2003 | Kästle |
| 6,654,624 | B2 | 11/2003 | Diab et al. |
| 6,658,276 | B2 | 12/2003 | Kianl et al. |
| 6,658,277 | B2 | 12/2003 | Wasserman |
| 6,662,033 | B2 | 12/2003 | Casciani et al. |
| 6,665,551 | B1 | 12/2003 | Suzuki |
| 6,668,182 | B2 | 12/2003 | Hubelbank |
| 6,668,183 | B2 | 12/2003 | Hicks et al. |
| 6,671,526 | B1 | 12/2003 | Aoyagi et al. |
| 6,671,528 | B2 | 12/2003 | Steuer et al. |
| 6,671,530 | B2 | 12/2003 | Chung et al. |
| 6,671,531 | B2 | 12/2003 | Al-Ali et al. |
| 6,671,532 | B1 | 12/2003 | Fudge et al. |
| 6,675,031 | B1 | 1/2004 | Porges et al. |
| 6,678,543 | B2 | 1/2004 | Diab et al. |
| 6,681,126 | B2 | 1/2004 | Solenberger |
| 6,681,128 | B2 | 1/2004 | Steuer et al. |
| 6,681,454 | B2 | 1/2004 | Modgil et al. |
| 6,684,090 | B2 | 1/2004 | Ali et al. |
| 6,684,091 | B2 | 1/2004 | Parker |
| 6,694,160 | B2 | 2/2004 | Chin |
| 6,697,653 | B2 | 2/2004 | Hanna |
| 6,697,655 | B2 | 2/2004 | Sueppel et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,699,199 | B2 | 3/2004 | Asada et al. |
| 6,701,170 | B2 | 3/2004 | Stetson |
| 6,702,752 | B2 | 3/2004 | Dekker |
| 6,707,257 | B2 | 3/2004 | Norris |
| 6,708,049 | B1 | 3/2004 | Berson et al. |
| 6,709,402 | B2 | 3/2004 | Dekker |
| 6,711,424 | B1 | 3/2004 | Fine et al. |
| 6,711,425 | B1 | 3/2004 | Reuss |
| 6,712,762 | B1 | 3/2004 | Lichter |
| 6,714,803 | B1 | 3/2004 | Mortz |
| 6,714,804 | B2 | 3/2004 | Al-Ali et al. |
| 6,714,805 | B2 | 3/2004 | Jeon et al. |
| RE38,492 | E | 4/2004 | Diab et al. |
| 6,719,686 | B2 | 4/2004 | Coakley et al. |
| 6,719,705 | B2 | 4/2004 | Mills |
| 6,720,734 | B2 | 4/2004 | Norris |
| 6,721,584 | B2 | 4/2004 | Baker, Jr. et al. |
| 6,721,585 | B1 | 4/2004 | Parker |
| 6,725,074 | B1 | 4/2004 | Kästle |
| 6,725,075 | B2 | 4/2004 | Al-Ali |
| 6,731,962 | B1 | 5/2004 | Katarow |
| 6,731,963 | B2 | 5/2004 | Finarov et al. |
| 6,731,967 | B1 | 5/2004 | Turcott |
| 6,735,459 | B2 | 5/2004 | Parker |
| 6,745,060 | B2 | 6/2004 | Diab et al. |
| 6,745,061 | B1 | 6/2004 | Hicks et al. |
| 6,748,253 | B2 | 6/2004 | Norris et al. |
| 6,748,254 | B2 | 6/2004 | O'Neil et al. |
| 6,754,515 | B1 | 6/2004 | Pologe |
| 6,754,516 | B2 | 6/2004 | Mannheimer |
| 6,760,607 | B2 | 7/2004 | Al-Ali |
| 6,760,609 | B2 | 7/2004 | Jacques |
| 6,760,610 | B2 | 7/2004 | Tschupp et al. |
| 6,763,255 | B2 | 7/2004 | DeLonzor et al. |
| 6,763,256 | B2 | 7/2004 | Kimball et al. |
| 6,770,028 | B1 | 8/2004 | Ali et al. |
| 6,771,994 | B2 | 8/2004 | Kiani et al. |
| 6,773,397 | B2 | 8/2004 | Kelly |
| 6,778,923 | B2 | 8/2004 | Norris et al. |
| 6,780,158 | B2 | 8/2004 | Yarita |
| 6,791,689 | B1 | 9/2004 | Weckstrom |
| 6,792,300 | B1 | 9/2004 | Diab et al. |
| 6,801,797 | B2 | 10/2004 | Mannheimer et al. |
| 6,801,798 | B2 | 10/2004 | Geddes et al. |
| 6,801,799 | B2 | 10/2004 | Mendelson |
| 6,801,802 | B2 | 10/2004 | Sitzman et al. |
| 6,802,812 | B1 | 10/2004 | Walker et al. |
| 6,805,673 | B2 | 10/2004 | Dekker |
| 6,810,277 | B2 | 10/2004 | Edgar, Jr. et al. |
| 6,813,511 | B2 | 11/2004 | Diab et al. |
| 6,816,741 | B2 | 11/2004 | Diab |
| 6,819,950 | B2 | 11/2004 | Mills |
| 6,822,564 | B2 | 11/2004 | Al-Ali |
| 6,825,619 | B2 | 11/2004 | Norris |
| 6,826,419 | B2 | 11/2004 | Diab et al. |
| 6,829,496 | B2 | 12/2004 | Nagai et al. |
| 6,830,711 | B2 | 12/2004 | Mills et al. |
| 6,836,679 | B2 | 12/2004 | Baker, Jr. et al. |
| 6,839,579 | B1 | 1/2005 | Chin |
| 6,839,580 | B2 | 1/2005 | Zonios et al. |
| 6,839,582 | B2 | 1/2005 | Heckel |
| 6,839,659 | B2 | 1/2005 | Tarassenko et al. |
| 6,842,635 | B1 | 1/2005 | Parker |
| 6,845,256 | B2 | 1/2005 | Chin et al. |
| 6,850,787 | B2 | 2/2005 | Weber et al. |
| 6,850,788 | B2 | 2/2005 | Al-Ali |
| 6,850,789 | B2 | 2/2005 | Schweitzer, Jr. et al. |
| 6,861,639 | B2 | 3/2005 | Al-Ali |
| 6,863,652 | B2 | 3/2005 | Huang et al. |
| 6,865,407 | B2 | 3/2005 | Kimball et al. |
| 6,879,850 | B2 | 4/2005 | Kimball |
| 6,882,874 | B2 | 4/2005 | Huiku |
| 6,898,452 | B2 | 5/2005 | Al-Ali et al. |
| 6,909,912 | B2 | 6/2005 | Melker et al. |
| 6,912,413 | B2 | 6/2005 | Rantala et al. |
| 6,920,345 | B2 | 7/2005 | Al-Ali et al. |
| 6,931,269 | B2 | 8/2005 | Terry |
| 6,934,570 | B2 | 8/2005 | Kiani et al. |
| 6,941,162 | B2 | 9/2005 | Fudge et al. |
| 6,947,781 | B2 | 9/2005 | Asada et al. |
| 6,950,687 | B2 | 9/2005 | Al-Ali |
| 6,954,664 | B2 | 10/2005 | Sweitzer |
| 6,968,221 | B2 | 11/2005 | Rosenthal |
| 6,979,812 | B2 | 12/2005 | Al-Ali |
| 6,983,178 | B2 | 1/2006 | Fine et al. |
| 6,985,763 | B2 | 1/2006 | Boas et al. |
| 6,985,764 | B2 | 1/2006 | Mason et al. |
| 6,990,426 | B2 | 1/2006 | Yoon et al. |
| 6,992,751 | B2 | 1/2006 | Okita et al. |
| 6,992,772 | B2 | 1/2006 | Block |
| 6,993,371 | B2 | 1/2006 | Kiani et al. |
| 6,993,372 | B2 | 1/2006 | Fine et al. |
| 6,996,427 | B2 | 2/2006 | Ali et al. |
| 7,003,338 | B2 | 2/2006 | Weber et al. |
| 7,003,339 | B2 | 2/2006 | Diab et al. |
| 7,006,855 | B1 | 2/2006 | Sarussi |
| 7,006,856 | B2 | 2/2006 | Baker, Jr. et al. |
| 7,016,715 | B2 | 3/2006 | Stetson |
| 7,020,507 | B2 | 3/2006 | Scharf et al. |
| 7,024,233 | B2 | 4/2006 | Ali et al. |
| 7,024,235 | B2 | 4/2006 | Melker et al. |
| 7,025,728 | B2 | 4/2006 | Ito et al. |
| 7,027,849 | B2 | 4/2006 | Al-Ali |
| 7,027,850 | B2 | 4/2006 | Wasserman |
| 7,039,449 | B2 | 5/2006 | Al-Ali |
| 7,043,289 | B2 | 5/2006 | Fine et al. |
| 7,047,055 | B2 | 5/2006 | Boas et al. |
| 7,060,035 | B2 | 6/2006 | Wasserman |
| 7,062,307 | B2 | 6/2006 | Norris et al. |
| 7,067,893 | B2 | 6/2006 | Mills et al. |

| Patent/Publication | Date | Name |
|---|---|---|
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,162,288 B2 | 1/2007 | Nordstrom et al. |
| 7,190,987 B2 | 3/2007 | Kindekugel et al. |
| 7,198,778 B2 | 4/2007 | Achilefu et al. |
| 7,215,984 B2 | 5/2007 | Diab et al. |
| 7,228,161 B2 | 6/2007 | Chin |
| 7,236,881 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,255,006 B2 | 8/2007 | Al-Ali et al. |
| 7,280,858 B2 | 10/2007 | Al-Ali et al. |
| 7,295,866 B2 | 11/2007 | Al-Ali |
| 7,305,262 B2 | 12/2007 | Brodnick et al. |
| 7,315,753 B2 | 1/2008 | Baker, Jr. et al. |
| 2002/0016537 A1 | 2/2002 | Muz et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0038082 A1 | 3/2002 | Chin |
| 2002/0042558 A1 | 4/2002 | Mendelson |
| 2002/0068859 A1 | 6/2002 | Knopp |
| 2002/0072681 A1 | 6/2002 | Schnall |
| 2002/0103423 A1 | 8/2002 | Chin et al. |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0109775 A1 | 6/2003 | O'Neil et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0199063 A1 | 10/2004 | O'Neil et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2005/0004479 A1 | 1/2005 | Townsend et al. |
| 2005/0014999 A1 | 1/2005 | Rahe-Meyer |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0070773 A1 | 3/2005 | Chin |
| 2005/0070775 A1 | 3/2005 | Chin et al. |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0090725 A1 | 4/2005 | Joseph et al. |
| 2005/0101851 A1 | 5/2005 | Chin |
| 2005/0197548 A1 | 9/2005 | Dietiker |
| 2005/0228248 A1 | 10/2005 | Dietiker |
| 2005/0256386 A1 | 11/2005 | Chan |
| 2005/0272986 A1 | 12/2005 | Smith |
| 2005/0277819 A1 | 12/2005 | Kiani et al. |
| 2006/0020179 A1 | 1/2006 | Anderson |
| 2006/0030764 A1 | 2/2006 | Porges |
| 2006/0058594 A1 | 3/2006 | Ishizuka et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0155198 A1 | 7/2006 | Schmid |
| 2006/0173257 A1 | 8/2006 | Nagai |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073125 A1 | 3/2007 | Hoarau et al. |
| 2007/0073126 A1 | 3/2007 | Raridan |
| 2007/0073128 A1 | 3/2007 | Hoarau |
| 2007/0078315 A1 | 4/2007 | Kling et al. |
| 2007/0078316 A1 | 4/2007 | Hoarau |
| 2007/0260129 A1 | 11/2007 | Chin |
| 2007/0260130 A1 | 11/2007 | Chin |
| 2007/0260131 A1 | 11/2007 | Chin |
| 2007/0299328 A1 | 12/2007 | Chin et al. |

FOREIGN PATENT DOCUMENTS

| | | |
|---|---|---|
| DE | 3516338 | 11/1986 |
| DE | 37 03 458 | 8/1988 |
| DE | 3938759 | 5/1991 |
| DE | 4210102 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 0135840 A | 4/1985 |
| EP | 00194105 | 9/1986 |
| EP | 00204459 | 12/1986 |
| EP | 0 262 779 | 4/1988 |

| | | | | | |
|---|---|---|---|---|---|
| EP | 0315040 | 10/1988 | JP | 10216114 | 8/1998 |
| EP | 0314331 | 5/1989 | JP | 10216115 | 8/1998 |
| EP | 00352923 | 1/1990 | JP | 10337282 | 12/1998 |
| EP | 0 360 977 | 4/1990 | JP | 11019074 | 1/1999 |
| EP | 00430340 | 6/1991 | JP | 11155841 | 6/1999 |
| EP | 0435 500 | 7/1991 | JP | 11 188019 | 7/1999 |
| EP | 0572684 | 5/1992 | JP | 11244268 | 9/1999 |
| EP | 00497021 | 8/1992 | JP | 20107157 | 4/2000 |
| EP | 0529412 | 8/1992 | JP | 20237170 | 9/2000 |
| EP | 0531631 | 9/1992 | JP | 21245871 | 9/2001 |
| EP | 0566354 | 4/1993 | JP | 22224088 | 8/2002 |
| EP | 0587009 | 8/1993 | JP | 22282242 | 10/2002 |
| EP | 00630203 | 9/1993 | JP | 23153881 | 5/2003 |
| EP | 0 572 684 | 12/1993 | JP | 23153882 | 5/2003 |
| EP | 00615723 | 9/1994 | JP | 23169791 | 6/2003 |
| EP | 00702931 | 3/1996 | JP | 23194714 | 7/2003 |
| EP | 00724860 | 8/1996 | JP | 23210438 | 7/2003 |
| EP | 00793942 | 9/1997 | JP | 23275192 | 9/2003 |
| EP | 0 864 293 | 9/1998 | JP | 23339678 | 12/2003 |
| EP | 01006863 | 10/1998 | JP | 24008572 | 1/2004 |
| EP | 01006864 | 10/1998 | JP | 24089546 | 3/2004 |
| EP | 0875199 | 11/1998 | JP | 24113353 | 4/2004 |
| EP | 00998214 | 12/1998 | JP | 24135854 | 5/2004 |
| EP | 0 898 933 | 3/1999 | JP | 24148069 | 5/2004 |
| EP | 0898933 | 3/1999 | JP | 24148070 | 5/2004 |
| EP | 01332713 | 8/2003 | JP | 24159810 | 6/2004 |
| EP | 01469773 | 8/2003 | JP | 24166775 | 6/2004 |
| EP | 1502529 | 7/2004 | JP | 24194908 | 7/2004 |
| EP | 01491135 | 12/2004 | JP | 24202190 | 7/2004 |
| FR | 2685865 | 1/1992 | JP | 24248819 | 9/2004 |
| GB | 2 259 545 | 3/1993 | JP | 24248820 | 9/2004 |
| JP | 63275325 | 11/1988 | JP | 24261364 | 9/2004 |
| JP | 2013450 | 1/1990 | JP | 24290412 | 10/2004 |
| JP | 2111343 | 4/1990 | JP | 24290544 | 10/2004 |
| JP | 02 191434 | 7/1990 | JP | 24290545 | 10/2004 |
| JP | 2237544 | 9/1990 | JP | 24329406 | 11/2004 |
| JP | 03 173536 | 7/1991 | JP | 24329607 | 11/2004 |
| JP | 3170866 | 7/1991 | JP | 24329928 | 11/2004 |
| JP | 3245042 | 10/1991 | JP | 24337605 | 12/2004 |
| JP | 4174648 | 6/1992 | JP | 24344367 | 12/2004 |
| JP | 4191642 | 7/1992 | JP | 24351107 | 12/2004 |
| JP | 4332536 | 11/1992 | JP | 25034472 | 2/2005 |
| JP | 3124073 | 3/1993 | WO | WO 98/09566 | 10/1989 |
| JP | 5049624 | 3/1993 | WO | WO 90/01293 | 2/1990 |
| JP | 5049625 | 3/1993 | WO | WO 90/04352 | 5/1990 |
| JP | 3115374 | 4/1993 | WO | WO 91/01678 | 2/1991 |
| JP | 05 200031 | 8/1993 | WO | WO 91/11137 | 8/1991 |
| JP | 2005/200031 | 8/1993 | WO | WO 92/00513 | 1/1992 |
| JP | 5212016 | 8/1993 | WO | WO 92/21281 | 12/1992 |
| JP | 06 014906 | 1/1994 | WO | WO 93/09711 | 5/1993 |
| JP | 06014906 | 1/1994 | WO | WO 93/13706 | 7/1993 |
| JP | 6016774 | 3/1994 | WO | WO 93/16629 | 9/1993 |
| JP | 3116255 | 4/1994 | WO | WO 94/03102 | 2/1994 |
| JP | 6029504 | 4/1994 | WO | WO 94/23643 | 10/1994 |
| JP | 6098881 | 4/1994 | WO | WO 95/02358 | 1/1995 |
| JP | 06 154177 | 6/1994 | WO | WO 95/12349 | 5/1995 |
| JP | 6269430 | 9/1994 | WO | WO 95/16970 | 6/1995 |
| JP | 6285048 | 10/1994 | WO | WO 96/13208 | 5/1996 |
| JP | 7001273 | 1/1995 | WO | WO 96/39927 | 12/1996 |
| JP | 7124138 | 5/1995 | WO | WO 97/36536 | 10/1997 |
| JP | 7136150 | 5/1995 | WO | WO 97/36538 | 10/1997 |
| JP | 3116259 | 6/1995 | WO | WO 97/49330 | 12/1997 |
| JP | 3116260 | 6/1995 | WO | WO 98/17174 | 4/1998 |
| JP | 7155311 | 6/1995 | WO | WO 98/18382 | 5/1998 |
| JP | 7155313 | 6/1995 | WO | WO 98/43071 | 10/1998 |
| JP | 3238813 | 7/1995 | WO | WO 98/51212 | 11/1998 |
| JP | 7171139 | 7/1995 | WO | WO 98/57577 | 12/1998 |
| JP | 3134144 | 9/1995 | WO | WO 99/00053 | 1/1999 |
| JP | 7236625 | 9/1995 | WO | WO 99/32030 | 7/1999 |
| JP | 7246191 | 9/1995 | WO | WO 99/47039 | 9/1999 |
| JP | 8256996 | 10/1996 | WO | WO 99/63884 | 12/1999 |
| JP | 9192120 | 7/1997 | WO | WO 00/21438 | 4/2000 |
| JP | 10216113 | 8/1998 | WO | WO 00/28888 | 5/2000 |

| | | |
|---|---|---|
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30th-Nov. 2nd, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK: pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximeter Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Atlanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitroing and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliabel Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokoo, et al.; "Artifact-Resistance, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI Number 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceeding of SPIE*, vol. 4431, pp. 260-265 (2001).

Gisiger, P.A., et al.; " OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insentivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; " Issues in the Laboratoy Evaluation of Pulse Oximeter Performances," *Anesth Analg.* vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients, " *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design For Home Health Care," *Proceedings of the Second Joint EMBS/BMES Conference*, Houston, Texas; Oct. 23-26, 2002; pp. 1871-1872.

Ericson, M.N.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment: Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference of Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recording using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo* (*Aritificial Respiration*), vol. 20, No. 1, pp. 24-29 (2003).

Lebak, J.W., et al.; "Implementation of a Standards-Based Pulse Oximeter on a Wearable, Embedded Platform," *Proceedings of the 25th Annual International Conference of the IEEE EMBS*, Cancun, Mexico, Sep. 17-21, 2003: pp. 3196-3198.

Nagl, L., et al.; "Wearable Sensor System for Wireless State-of-Health Determination in Cattle," *Proceedings of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodectector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry with Near Infrared Laser Diodes," *IMTC 2004—Instrumentation and Measurement Technology Conference*, Como, Italy, May 18-20, 2004; pp. 718-723.

Suginao, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*. San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistance Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broaded Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

* cited by examiner

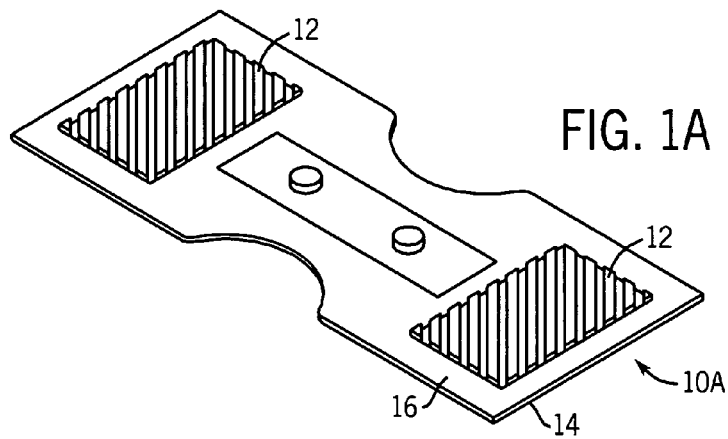
FIG. 1A
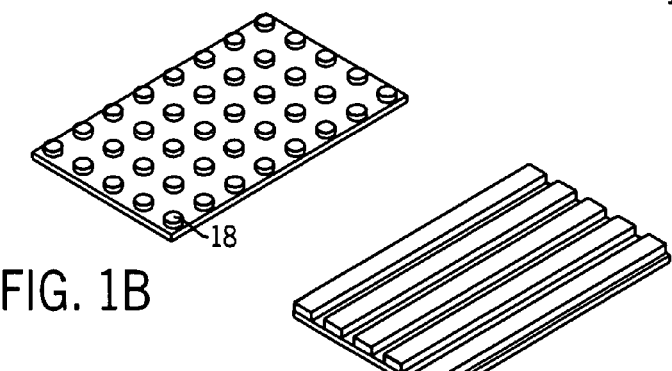
FIG. 1B
FIG. 1C
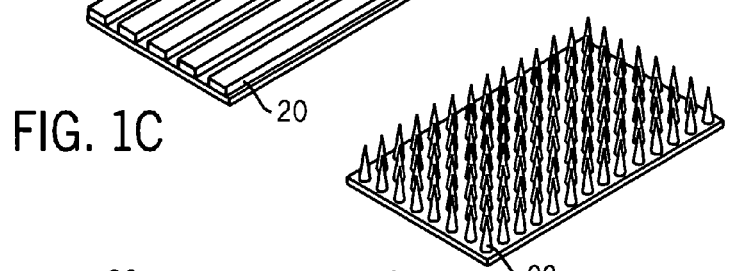
FIG. 1D
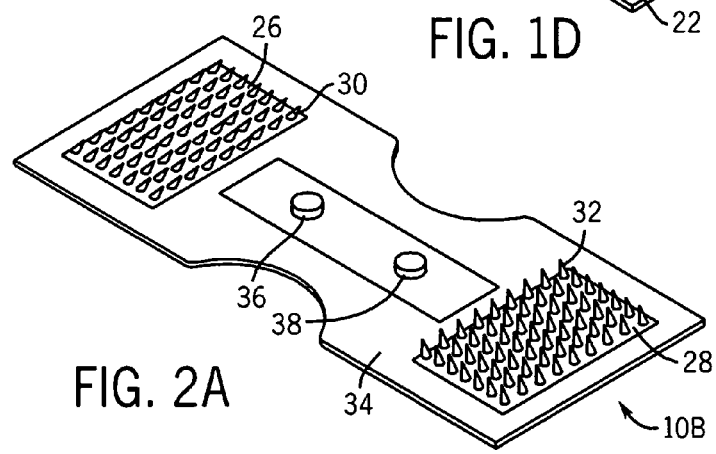
FIG. 2A

MEDICAL SENSOR AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Accurate pulse oximetry measurements depend on the secure placement of a sensor on the desired measurement site on a patient's skin. Pulse oximetry sensors are typically either disposable bandage-type structures that attach the sensor components to the patient with adhesive materials, or reusable clip-type devices that affix the sensor components in place with tension provided by a spring. Regardless of the type of sensor used, the sensor should fit snugly enough that incidental patient motion will not dislodge the sensor, yet not so tight that normal blood flow is disrupted, which may interfere with pulse oximetry measurements. Furthermore, lack of a secure fit may allow ambient light to reach the photodetecting elements of the sensor, thus introducing error into the pulse oximetry measurements. Additionally, sensor movement may lead to motion artifacts, another potential source of measurement error.

Pulse oximetry sensors are used in emergency room and trauma center settings where the sensor may be exposed to liquids and/or bodily fluids. A patient's sweat or blood, for example, may interfere with the ability of adhesive bandages to adhere to the skin. Further, reusable sensors are subject to frequent repositioning, which may lead to weakening of the mechanical components of a clip-style sensor. Thus, an improved securing mechanism may be desirable.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; at least one sensing element disposed on the sensor body; and a non-adhesive gripping portion having raised protrusions disposed on a tissue-contacting surface of the sensor body.

There is also provided a pulse oximetry system that includes a pulse oximetry monitor and a pulse oximetry sensor adapted to be operatively coupled to the monitor. The sensor includes a sensor body; at least one sensing element disposed on the sensor body; and a non-adhesive gripping portion having raised protrusions disposed on a tissue-contacting surface of the sensor body.

There is also provided a method of operating a sensor that includes: contacting a patient's skin with a non-adhesive gripping portion having raised protrusions of a sensor body; emitting light from an emitter disposed on the sensor body; and detecting the light with a detector disposed on the sensor body.

There is also provided a method of manufacturing a sensor that includes: providing a sensor body, wherein a non-adhesive gripping portion having raised protrusions is disposed on a tissue-contacting surface of the sensor body; and providing at least one sensing element disposed on the sensor body.

BRIEF DESCRIPTION OF THE DRAWINGS

Advantages of the invention may become apparent upon reading the following detailed description and upon reference to the drawings in which:

FIG. 1A illustrates a perspective view of an embodiment of an exemplary bandage-type pulse oximetry sensor with non-adhesive gripping regions according to the present invention;

FIGS. 1B-D illustrate alternate embodiments of non-adhesive gripping portions;

FIG. 2A illustrates an embodiment of an exemplary bandage-type pulse oximetry sensor with directional non-adhesive gripping regions according to the present invention;

DETAILED DESCRIPTION OF SPECIFIC EMBODIMENTS

Figure 2B:
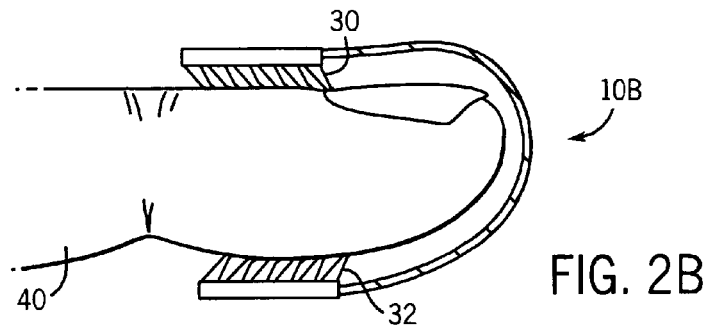
FIG. 2B illustrates a cross-sectional view of the pulse oximetry sensor of FIG. 3A applied to a patient's finger.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present techniques, the exemplary medical sensors described below may be used for pulse oximetry or other spectrophotometric uses. The techniques described below reduce sensor movement by providing a durable, non-adhesive gripping contact with a patient's skin.

Pulse oximetry sensors are typically placed on a patient in a location that is normally perfused with arterial blood to facilitate measurement of the desired blood characteristics, such as arterial oxygen saturation measurement ($SpO_2$). Common sensor placement sites include a patient's fingertips, toes, forehead, or earlobes. Regardless of the location of the sensor, it is often desirable to provide a secure attachment of the sensor to a patient's skin.

Several factors may affect the ability of the sensor to firmly attach to the sensor site. Sensors are generally worn for several hours before being removed or repositioned. Thus, a patient may sweat or bleed in the area of the tissue covered by the sensor, creating a slick surface that promotes sliding of the sensor relative to the skin. Additionally, when a sensor is repositioned every few hours, as typically recommended, each application weakens the adhesiveness of any adhesive bandages, as well as the spring force of any mechanical components of the sensor.

Sensors as described herein may include an emitter and a detector that may be of any suitable type. For example, the emitter may be one or more light emitting diodes adapted to transmit one or more wavelengths of light in the red to infrared range, and the detector may be a photodetector selected to receive light in the range or ranges emitted from the emitter. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

The sensors disclosed herein include a non-adhesive gripping portion to provide a securing mechanism and to reduce sensor movement after application of the sensor to the patient. The non-adhesive gripping portions described below in relation to the exemplary embodiments may be constructed from any suitable material that functions to provide additional gripping strength between the sensor 10 and the patient's tissue. For example, a suitable non-adhesive gripping portion may be made of plastic, rubber, silicone, vinyl, or woven material. For example, the non-adhesive gripping portion may be a relatively thin, flexible material such as Super Grip® Easy Liner® (Henkel) that is disposed on the tissue-contacting surface of the sensor 10. As described below in certain embodiments, the non-adhesive gripping portion may be integrally constructed with the sensor 10, for example molded onto the tissue-contacting surface. In other embodiments, the non-adhesive gripping portion may be a separate component. As described below, it may be advantageous to apply a removable non-adhesive gripping portion to a reusable sensor, so that the non-adhesive gripping portion may be detached and replaced multiple times.

In certain embodiments, a non-adhesive gripping portion comprises a material that has a relatively large static coefficient of friction. A material with a large static coefficient of friction helps to keep sensor stable relative to the skin as a patient moves. According to the present techniques, the static coefficient of friction of a material may be tested using the following procedure: (1) Attach a protractor to a vertical wall with the center in line with the edge of a table. (2) Set up a stop block at the edge of the table to act as a pivot point for a glass plate. (3) Place the glass plate flat on the table with one edge along the edge of the table, up against the stop block. (4) Place a test sample of the material on the glass plate. (5) Lift the free edge of the glass plate until the test sample just starts to slip. (6) Record angle at which slippage first occurred. This angle is the angle of repose. Then calculate the coefficient of friction, which is the tangent of the angle of repose.

The static coefficient of friction for a non-adhesive gripping portion may greater than 10. In certain embodiments, the static coefficient of friction for a non-adhesive gripping portion may be greater than 100. A non-adhesive gripping portion may be a material that has a high static coefficient of friction relative to glass, such as polyvinyl chloride (PVC) foam.

One with skill in the art realizes that a static coefficient of friction calculated as described above is relative to a glass plate, and that other materials may be used as a reference point. For example, it may be desirable to calculate a static coefficient of friction of a material relative to a patient's skin. In certain embodiment, the non-adhesive gripping portion has a static coefficient of friction greater than 5 with respect to a patient's skin.

FIG. 1A illustrates an exemplary transmission-type bandage sensor appropriate for use on a patient's digit. As shown in FIG. 1A, a sensor 10A may have non-adhesive gripping portions 12 that are disposed on a conformable sensor body 14 on a tissue-contacting surface 16. The non-adhesive gripping portions 12 may have a texture. The texture may be visible to the unaided eye, or alternatively it may be a microtexture that is not visible to the unaided eye. The non-adhesive gripping portions 12 are characterized by a surface that provides frictional resistance when in contact with the patient's skin. In other embodiments, as shown in FIGS. 1B-D, the non-adhesive gripping portions 12 may contain raised protrusions, such as nubs 18 (FIG. 1B), ridges 20 (FIG. 1C) or barbs 22 (FIG. 1D).

The raised protrusions may be conformable or semi-rigid. For example, the barbs 22 may be conformable to avoid causing discomfort for the patient. Generally, it is envisioned that the raised protrusions may protrude at least about 0.1 mm from the surface of the sensor body. The raised protrusions may be rubber, silicone, or plastic. In certain embodiments, the raised protrusions may be formed from any suitable material with a durometer hardness ranging from 20-90 Shore D.

In situations in which a patient is ambulatory and is being continuously monitored, it may be desirable to affix a sensor 10 to the patient with sufficient gripping strength to prevent dislodgement resulting from everyday activity. FIG. 2A illustrates a bandage-type sensor 10B in which the conformable sensor body 24 contains directional non-adhesive portions 26 and 28 with angled barbs 30 and 32. The directional non-adhesive portions 26 and 28 are disposed on the tissue-contacting surface 34 of the conformable sensor body 26 such that the angled barbs 30 and 32 are oriented toward the emitter 36 and detector 38. As shown in FIG. 2B, when the sensor 10B is applied to a patient's digit 40, the angled barbs 30 and 32 are oriented such that the sensor 10B is resistant to being pulled off the digit 40. Thus, the sensor 10B remains relatively secure if a patient wishes to be able to use his or her hands to type on a keyboard, for example.

Figure 3:
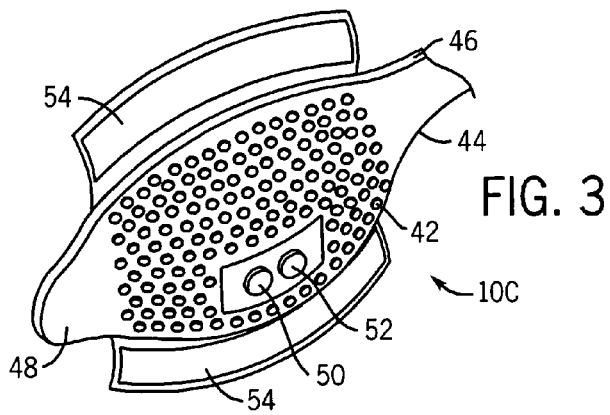
FIG. 3 illustrates a perspective side view of an embodiment of an exemplary forehead pulse oximetry sensor according to the present invention.

It may be desirable to limit the use of adhesive materials on skin that is particularly fragile, such as that of a newborn infant. FIG. 3 illustrates an alternate embodiment in which a forehead sensor 10C has nubs 42 disposed on a tissue-contacting surface 44 of a sensor body 46. The sensor 10C has a finger-lift portion 48 that does not contain the nubs to allow for ease of sensor 10C removal. The nubs 42 protrude sufficiently to allow the sensor 10C to grip the forehead, but are not so elevated as to interfere with close contact of the emitter 50 and detector 52 with the skin. The sensor 10C has adhesive bandages 54 disposed around the perimeter of the sensor body 46. Such a configuration minimizes the use of adhesive bandages 54 while retaining adequate gripping to allow normal use of the sensor 10C. Because the area of skin surface contacted by adhesive is smaller as compared to a conventional sensor, there is a reduced risk of skin damage caused by the adhesive bandages 54. As depicted, the region containing the raised nubs 42 is at least 50% of the tissue-contacting surface 44 of the sensor 10C.

In other embodiments, the percentage of a tissue-contacting surface 44 of a sensor containing a non-adhesive gripping portion may vary depending on the activity level of the patient wearing the sensor, and the amount of adhesive bandages 54 used. In certain embodiments, it is contemplated that the surface area of a sensor that contains raised protrusions is inversely proportional to the amount of adhesive used. That is, if a sensor has raised protrusions on over half of its surface area, fewer adhesive bandages may be used in order to achieve a desirable level of frictional resistance to sensor movement. In certain embodiments, a non-adhesive gripping portion may be at least about 10%, and typically in a range from about 10% to about 95% of the tissue-contacting area of the sensor.

However, it should be understood that a very small surface area containing raised protrusions, such as nubs 42, may be effective at providing almost adhesive levels of gripping to the skin if placed on the sensor in areas that are prone to movement. For example, it may be desirable to design a finger sensor with a non-adhesive gripping portion in areas of a finger that are likely to move, such as joints.

Figure 4A:
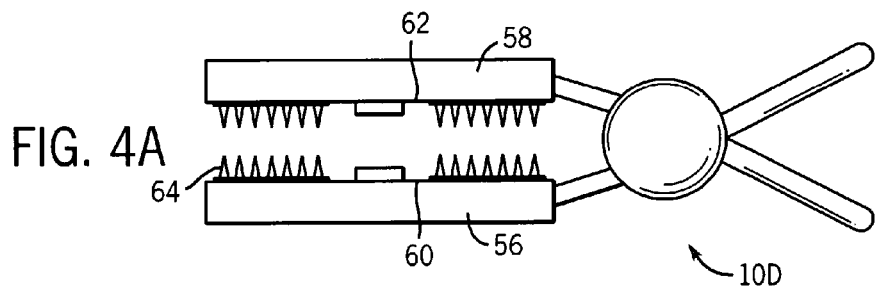
FIG. 4A illustrates a cross-sectional view of an embodiment of an exemplary clip-style pulse oximetry sensor according to the present invention.
Figure 4B:
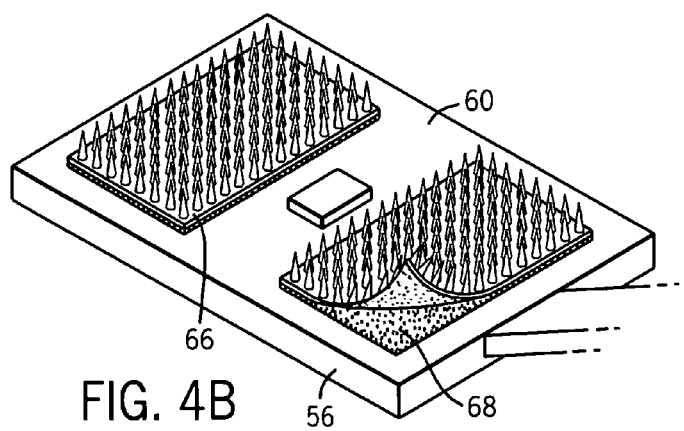
FIG. 4B illustrates a perspective view of the clip-style pulse oximetry sensor of FIG. 4A in which the non-adhesive gripping portion is removable.

Although the previously discussed embodiments have described conformable bandage-type sensors, it is also envisioned that similar advantages may be realized with relatively rigid clip-type sensors. For example, FIG. 4A shows a clip-type sensor 10D adapted to be applied to a patient's earlobe. The sensor 10D has portions 56 and 58 having tissue-contacting surfaces 60 and 62, on which raised barbs 64 are disposed. The barbs 64 grip the skin of the earlobe and resist movement of the sensor due to patient movement or gravity. As clip-type sensors are generally reusable, they are cleaned in between uses. Thus, it may be advantageous to be able to remove the barbs 64 for disposal, as their complex surfaces may trap dirt and sweat, thus making them difficult to clean. It is envisioned that the barbs 64 may be disposed on the tissue-contacting surfaces 60 and 62 on a backing 66 that is attached to the sensor body with a snap or other mechanism. In other embodiments, it may be appropriate to use a hook and loop faster 68, as shown in FIG. 4B. Thus, the barbs 64 may be easily peeled off and replaced by a healthcare worker.

Figure 5:
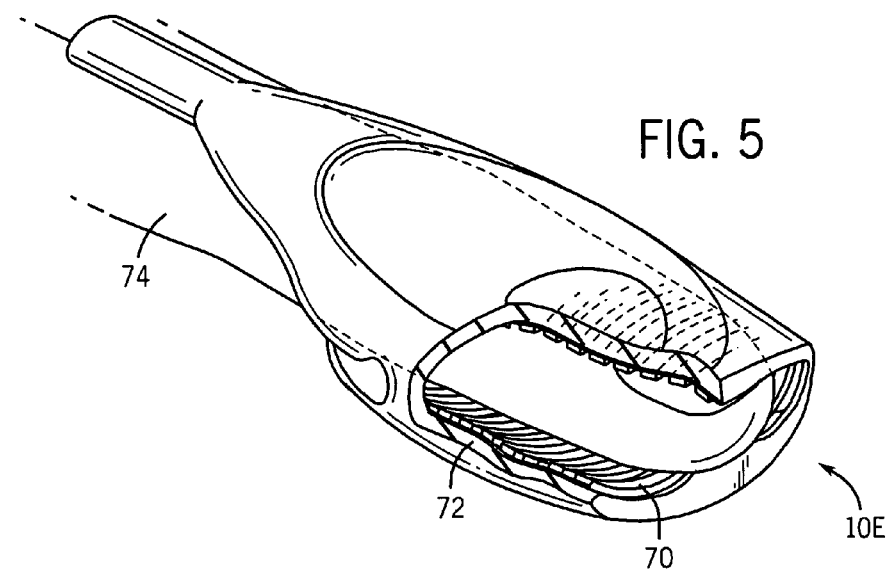
FIG. 5 illustrates an embodiment of an exemplary molded pulse oximetry sensor with an integral non-adhesive gripping portion according to the present invention.

In some instances, for cost and/or convenience, it may be desirable to manufacture sensors from a single mold. FIG. 5 illustrates an alternate embodiment in which a flexible molded slip-on type sensor 10E has integrally constructed molded ridges 70 disposed on a tissue-contacting surface 72. The sensor 10E is held on a patient's digit 74 by a combination of tension provided by the geometry and material of the sensor 10E and the gripping strength provided by ridges 70. The ridges 70 provide a mechanism for resisting movement of the sensor 10E relative to the digit 74. The ridges 70 are depicted as being orthogonally oriented to the digit 74 when the sensor 10E is applied to the patient. Thus, the frictional force of the ridges 70 opposes sliding of the digit 74 out of the sensor 10E. The ridges 70 may follow the contour of the digit 74, rising or falling in height to accommodate joints or finger pads. Since the ridges 70 are formed by molding, changes in the design of the sensor mold could easily accommodate a variety of arrangements of the ridges 70. For example, a wider spacing between ridges 70 may allow for ease in cleaning the sensor 10E between applications.

Figure 6A:
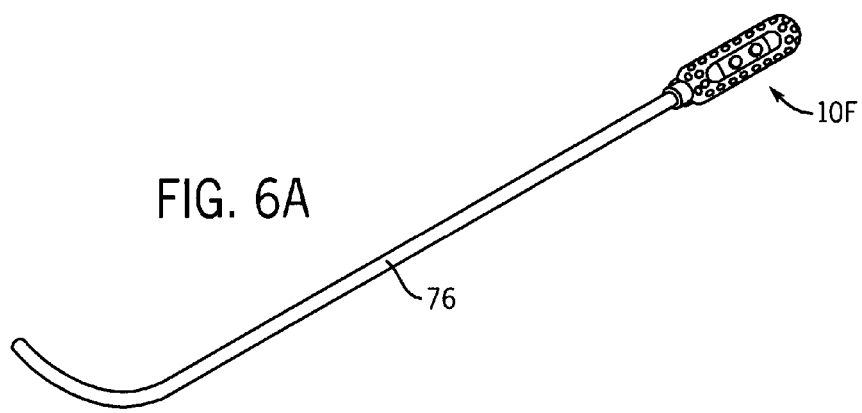
FIG. 6A illustrates a perspective view of an embodiment of a fetal pulse oximetry sensor with a non-adhesive gripping portion according to the present invention.
Figure 6B:
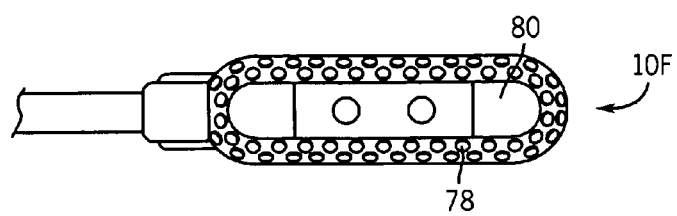
FIG. 6B illustrates an enlarged view of the sensor of FIG. 6A.

Sensors designed in accordance with the present techniques may provide advantages in liquid environments such as the uterus, in which the use of adhesives is not possible. In many instances, physicians wish to employ an intrauterine sensor to monitor physiological characteristics of a fetus, particularly during childbirth. An exemplary sensor 10F for intrauterine use is depicted in FIG. 6A. The sensor 10F is adapted to include a non-adhesive gripping portion 78 to assist the user in gripping the fetus' skin. The sensor 10F is normally manually introduced into the uterus and positioned against the fetus' head with a long, flexible handle 76 to allow proper placement of the sensor 10F. Fetal sensors, once properly positioned, may be held in place by a healthcare worker or by the pressure of the sensor 10F against the uterine walls for the checking of fetal blood oxygen. In other embodiments (not shown), the sensor 10F may be temporarily attached to the fetus' head with screws or other mechanisms. As illustrated in an enlarged view of the sensor body in FIG. 6B, the intrauterine fetal sensor 10F has a non-adhesive gripping portion 78 disposed around the perimeter of the tissue-contacting surface 80. The non-adhesive gripping portion 78 reduces movement of the sensor relative to the fetus' head, which may reduce motion artifacts.

Figure 7:
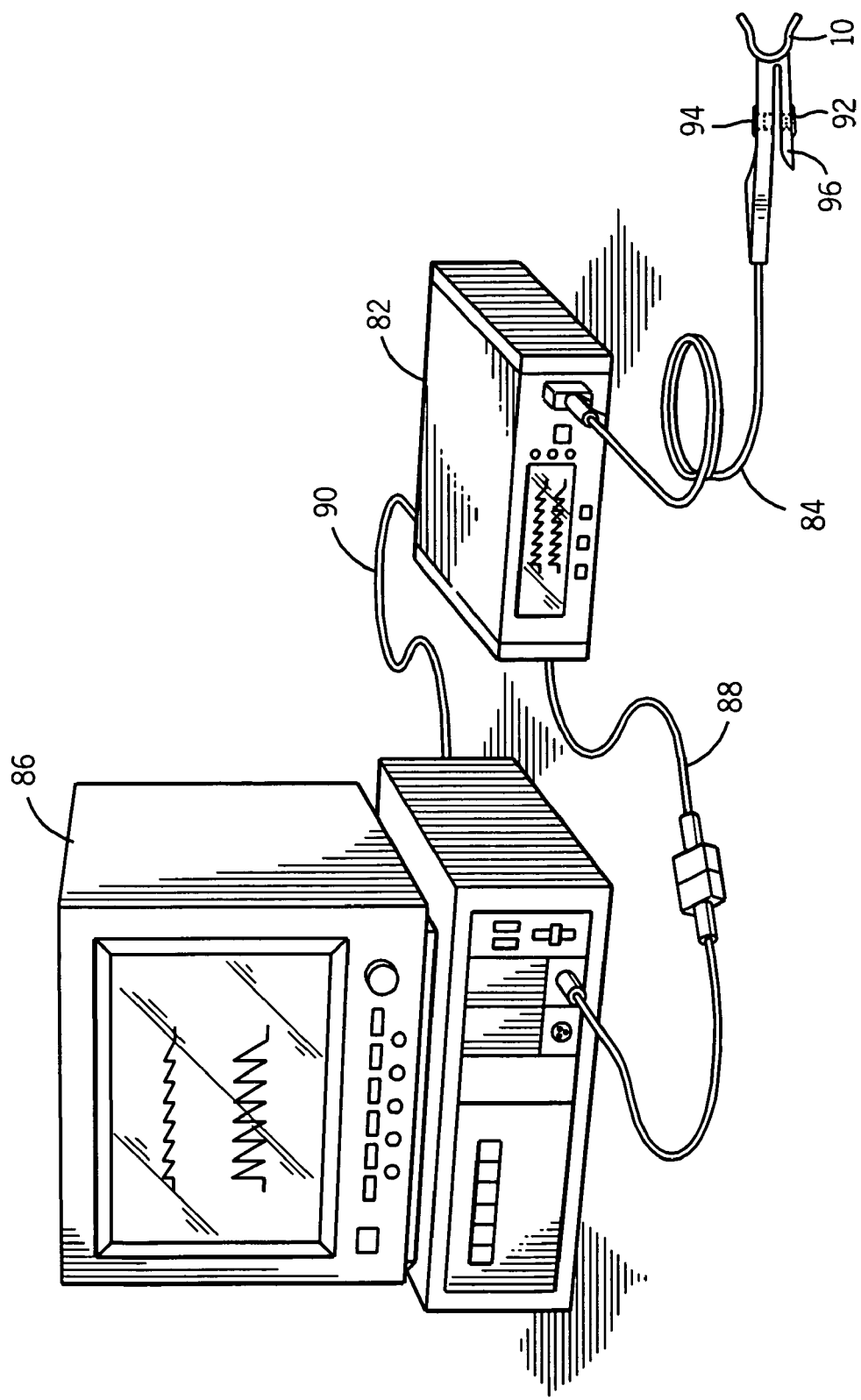
FIG. 7 illustrates a pulse oximetry system coupled to a multi-parameter patient monitor and a sensor according to embodiments of the present invention.

Sensors designed in accordance with the present techniques, such as the exemplary sensors described above, illustrated generically as a sensor 10, may be used in conjunction with a pulse oximetry monitor 82, as illustrated in FIG. 7. It should be appreciated that the cable 84 of the sensor 10 may be coupled to the monitor 82 or it may be coupled to a transmission device (not shown) to facilitate wireless transmission between the sensor 10 and the monitor 82. The monitor 82 may be any suitable pulse oximeter, such as those available from Nellcor Puritan Bennett Inc. Furthermore, to upgrade conventional pulse oximetry provided by the monitor 82 to provide additional functions, the monitor 82 may be coupled to a multi-parameter patient monitor 86 via a cable 88 connected to a sensor input port or via a cable 90 connected to a digital communication port.

The emitter 92 and the detector 94 may be disposed on a sensor body 96, which may be made of any suitable material, such as plastic, rubber, silicone, foam, woven material, or paper. Alternatively, the emitter 92 and the detector 94 may be remotely located and optically coupled to the sensor 10 using optical fibers. In the depicted embodiments, the sensor 10 is coupled to a cable 84 that is responsible for transmitting electrical and/or optical signals to and from the emitter 92 and detector 94 of the sensor 10. The cable 84 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 92 and detector 94 that are typically placed on opposing sides of the sensor site. If the sensor site is a fingertip, for example, the sensor 10 is positioned over the patient's fingertip such that the emitter 92 and detector 94 lie on either side of the patient's nail bed. In other words, the sensor 10 is positioned so that the emitter 92 is located on the patient's fingernail and the detector 94 is located 180° opposite the emitter 92 on the patient's finger pad. During operation, the emitter 92 shines one or more wavelengths of light through the patient's fingertip and the light received by the detector 94 is processed to determine various physiological characteristics of the patient. In each of the embodiments discussed herein, it should be understood that the locations of the emitter 92 and the detector 94 may be exchanged. For example, the detector 94 may be located at the top of the finger and the emitter 92 may be located underneath the finger. In either arrangement, the sensor 10 will perform in substantially the same manner.

Reflectance type sensors generally operate under the same general principles as transmittance type sensors. However, reflectance type sensors include an emitter 92 and detector 94 that are typically placed on the same side of the sensor site. For example, a reflectance type sensor may be placed on a patient's fingertip or forehead such that the emitter 92 and detector 94 lie side-by-side. Reflectance type sensors detect light photons that are scattered back to the detector 94.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents using principles of pulse oximetry. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A sensor compprising:
    a conformable bandage-style sensor body adapted to be placed on a patient's finger;
    at least one sensing element disposed on the sensor body; and
    a non-adhesive gripping portion having raised protrusions relative to a non-raised area disposed on a tissue-contacting surface of the sensor body, wherein the raised protrusions and the non-raised area of the non-adhesive gripping portion are capable of engaging a patient's tissue.

2. The sensor, as set forth in claim 1, wherein the sensor comprises at least one of a pulse oximetry sensor or a sensor for measuring a water fraction.

3. The sensor, as set forth in claim 1, wherein the at least one sensing element comprises an emitter and a detector.

4. The sensor, as set forth in claim 3, wherein the emitter comprises at least one light emitting diode, and wherein the detector comprises at least one photodetector.

5. The sensor, as set forth in claim 1, wherein the non-adhesive gripping portion comprises plastic, rubber, silicone, or vinyl.

6. The sensor, as set forth in claim 1, wherein the non-adhesive gripping portion is disposed on at least 50% of the tissue-contacting surface of the sensor body.

7. The sensor, as set forth in claim 1, wherein the raised protrusions comprise barbs, nubs, or ridges.

8. The sensor, as set forth in claim 1, wherein the non-adhesive gripping portion is directional.

9. The sensor, as set forth in claim 1, wherein the non-adhesive gripping portion is disposed on greater than 10% of the tissue-contacting surface of the sensor body.

10. The sensor, as set forth in claim 1, wherein the sensor comprises an adhesive disposed on the tissue-contacting surface of the sensor body.

11. The sensor, as set forth in claim 1, wherein the nonadhesive gripping portion comprises a material having a hardness ranging from 20-90 Shore D.

12. The sensor, as set forth in claim 1, wherein the non-adhesive gripping portion is disposed on the sensor body in an area corresponding to a finger joint when the sensor is placed on the patient's finger.

13. The sensor, as set forth in claim 1, wherein the non-adhesive gripping portion comprises a material having a static coefficient of friction greater than 100.

14. A pulse oximetry system comprising:
    a pulse oximetry monitor; and
    a pulse oximetry sensor adapted to be operatively coupled to the monitor, the sensor comprising:
        a conformable bandage-style sensor body adapted to be placed on a patient's finger;
        at least one sensing element disposed on the sensor body; and
        a non-adhesive gripping portion having raised protrusions relative to a non-raised area disposed on a tissue-contacting surface of the sensor body, wherein the raised protrusions and the non-raised area of the non-adhesive gripping portion are capable of engaging a patient's tissue.

15. The pulse oximetry system, as set forth in claim 14, wherein the sensor comprises a sensor for measuring a water fraction.

16. The pulse oximetry system, as set forth in claim 14, wherein the at least one sensing element comprises an emitter and a detector.

17. The pulse oximetry system, as set forth in claim 16, wherein the emitter comprises at least one light emitting diode, and wherein the detector comprises at least one photodetector.

18. The pulse oximetry system, as set forth in claim 14, wherein the non-adhesive gripping portion comprises plastic, rubber, silicone, or vinyl.

19. The pulse oximetry system, as set forth in claim 14, wherein the non-adhesive gripping portion is disposed on at least 50% of the tissue-contacting surface of the sensor body.

20. The pulse oximetry system, as set forth in claim 14, wherein the raised protrusions comprise barbs, nubs, or ridges.

21. The pulse oximetry system, as set forth in claim 14, wherein the non-adhesive gripping portion is directional.

22. The pulse oximetry system, as set forth in claim 14, wherein the non-adhesive gripping portion is disposed on greater than 10% of the tissue-contacting surface of the sensor body.

23. The pulse oximetry system, as set forth in claim 14, wherein the sensor comprises an adhesive disposed on the tissue-contacting surface of the sensor body.

24. The pulse oximetry system, as set forth in claim 14, wherein the non-adhesive gripping portion comprises a material having a hardness ranging from 20-90 Shore D.

25. The pulse oximetry system, as set forth in claim 14, wherein the non-adhesive gripping portion is disposed on the sensor body in an area corresponding to a finger joint when the sensor is placed on the patient's finger.

26. The pulse oximetry system, as set forth in claim 14, wherein the non-adhesive gripping portion comprises a material having a static coefficient of friction greater than 100.

27. A method comprising:
   contacting a patient's finger with a non-adhesive gripping portion of a conformable bandage-style sensor body, the gripping portion having raised protrusions relative to a non-raised area, wherein the raised protrusions and the non-raised area are adapted to engage a patient's tissue;
   emitting light from an emitter disposed on the sensor body into the patient's finger;
   detecting the light with a detector disposed on the sensor body; and
   providing a signal related to the detected light.

28. The method, as set forth in claim 27, wherein contacting comprises contacting the patient's finger with a plastic, rubber, silicone, or vinyl non-adhesive gripping portion.

29. The method, as set forth in claim 27, wherein contacting comprises contacting the patient's finger with barbs, nubs, or ridges.

30. The method, as set forth in claim 27, wherein contacting comprises contacting the patient's finger with a directional non-adhesive gripping portion.

31. The method, as set forth in claim 27, wherein contacting comprises contacting the patient's finger with an adhesive disposed on the sensor body.

32. A method of manufacturing a sensor, comprising:
   providing a conformable bandage-style sensor body adapted to be placed on a patient's finger; and
   providing a non-adhesive gripping portion comprising raised protrusions relative to a non-raised area disposed on a tissue-contacting surface of the sensor body, wherein the raised protrusions and the non-raised area are adapted to engage a patient's tissue; and
   providing at least one sensing element disposed on the sensor body.

33. The method, as set forth in claim 32, wherein providing at least one sensing element comprises providing an emitter and a detector.

34. The method, as set forth in claim 32, comprising:
   providing barbs, nubs, or ridges on the non-adhesive gripping portion.

35. The method, as set forth in claim 32, wherein the non-adhesive gripping portion comprises plastic, rubber, silicone, or vinyl.

36. The method, as set forth in claim 32, wherein the non-adhesive gripping portion is directional.

37. The method, as set forth in claim 32, comprising:
   providing the non-adhesive gripping portion on greater than 10% of the tissue-contacting surface of the sensor body.

38. The method, as set forth in claim 32, comprising:
   providing the non-adhesive gripping portion on greater than 50% of the tissue-contacting surface of the sensor body.

39. The method, as set forth in claim 32, comprising:
   providing an adhesive disposed on the tissue-contacting surface of the sensor body.

* * * * *